United States Patent
Halloran

[11] Patent Number: 6,071,975
[45] Date of Patent: Jun. 6, 2000

[54] METHOD OF PREPARING SILICONE OIL-IN-WATER MICROEMULSIONS

[75] Inventor: Daniel Joseph Halloran, Midland, Mich.

[73] Assignee: Dow Corning Corporation, Midland, Mich.

[21] Appl. No.: 09/227,838

[22] Filed: Jan. 11, 1999

[51] Int. Cl.$^7$ ............... B01J 13/00; A61K 7/075; C08L 43/04
[52] U.S. Cl. ............ 516/58; 424/70.12; 424/70.24; 424/70.28; 514/938; 516/67; 524/806
[58] Field of Search ............ 516/58, 67; 524/806; 424/70.12, 70.24, 70.28; 514/938

[56] References Cited

U.S. PATENT DOCUMENTS

| | | |
|---|---|---|
| 2,891,920 | 6/1959 | Hyde et al. . |
| 4,472,291 | 9/1984 | Rosano ................... 516/58 X |
| 4,999,398 | 3/1991 | Graiver et al. ............ 524/837 |
| 5,152,924 | 10/1992 | Gee ....................... 516/67 X |
| 5,518,716 | 5/1996 | Riccio et al. ............ 516/67 X |
| 5,684,085 | 11/1997 | Gee et al. ............ 424/70.12 X |
| 5,817,714 | 10/1998 | Graiver et al. ............ 524/762 |
| 5,969,038 | 10/1999 | Fecht et al. ............ 424/70.12 X |

*Primary Examiner*—Richard D. Lovering
*Attorney, Agent, or Firm*—James L. De Cesare

[57] ABSTRACT

A classical method of microemulsion formation involves mixing an oil and water with a surfactant (S1), and a co-surfactant (S2). The oil is mostly preferably a cyclic siloxane. The oil is added to a solution of the surfactant (S1) and water. A two-phase system containing the siloxane results. The two-phase system is then titrated with co-surfactant (S2) until a clear isotropic microemulsion results. An emulsion polymerization catalyst is added to the clear isotropic microemulsion, and polymerization of the cyclic siloxane is initiated. The polimerization is allowed to advance until the reaction is complete, or desired degree of polymerization (DP) has been obtained. Microemulsions of high molecular weight silicone polymers with low polydispersity can be produced.

13 Claims, No Drawings

METHOD OF PREPARING SILICONE OIL-IN-WATER MICROEMULSIONS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention is directed to thermodynamically stable, clear, single phase, silicone oil-in-water microemulsions. These optically clear one phase microemulsions are useful in many personal care applications, especially as deodorant or skin care lotions, and for delivering lipid soluble perfumes. In addition, the microemulsions can be used as a source of very small, i.e., below 10 nanometer (nm), droplets of silicone oil, for use in textile finishing, and as an additive in a hair conditioning product such as a shampoo. They also provide an alternative to the more volatile types of solvents typically used for diluting silicone oils. Because they exist as a single phase, the microemulsions are much easier to process.

BACKGROUND OF THE INVENTION

It is well documented (U.S. Pat. Nos. 4,999,398 and 5,817,714) that emulsions, especially silicone emulsions, are opaque, cloudy, and tend to separate on standing. Microemulsions, in contrast, are desirable, because they are thermodynamically stable, and contain equilibrium microstructures that are smaller than typical emulsion droplets. Thus, microemulsion products are generally indefinitely stable, and they can be optically clear.

As used herein, the term emulsion or macroemulsion means a mixture of one immiscible liquid in another, in the form of droplets, with diameters approximately in the range of 100–1,000 nanometer (0.1–1.0 micron/1,000–10,000 angstrom Å). In contrast, a microemulsion means a single or one phase transparent, thermodynamically stable, mixture of two or more immiscible liquids, and one or more surfactant(s) and co-surfactant(s).

In order to avoid confusion, it should be noted that the term microemulsion has been used loosely in the literature to describe any transparent composition containing water, oil and a surfactant, including compositions which are transparent by virtue of a very small structure size, and index of refraction matching.

However, it is almost always apparent from the details of the preparation given, which type of composition is in fact being made, considering the order of addition of the components, their polymerization, or when high energy mixing is involved.

Microemulsions, on the other hand, are generally always clear or transparent, because they contain structures smaller than the wavelength of visible light, typically of the order of magnitude of about 500 nanometer. Furthermore, a microemulsion, as that term is used herein, contains structures that are spontaneously self-assembled aggregates, consisting of oil and surfactant monolayers, or water and surfactant monolayers.

Although there are distinct domains present which are composed of water and oil, these types of systems can be properly described as being in the form of one phase, because the domains consist of molecular aggregates that spontaneously self-assemble.

A microemulsion may contain oil droplets dispersed in water (O/W), water droplets dispersed in oil (W/O), or it may be in the form of a bicontinuous structure or other structure. It can be recognized by several inherent characteristics which are (i) that it contains oil, water, and a surfactant; (ii) there is a high concentration of surfactant relative to oil; (iii) the system is optically clear; (iv) the phases do not separate by centrifugation; and (v) the system forms spontaneously.

For purposes of this invention, therefore, an emulsion is considered as containing structures having an average diameter of more than 100 nanometer (0.1 micron/1,000 angstrom Å), whereas a microemulsion contains structures having an average diameter of less than 100 nanometer (0.1 micron/1,000 angstrom Å), preferably less than 50 nanometer (0.05 micron/500 angstrom Å), and most preferably less than 10 nanometer (0.01 micron/100 angstrom Å). Microemulsion containing structures having an average diameter of as small as 5 nanometer (0.005 micron/50 angstrom Å) is also contemplated herein.

Clarity or transparency is controlled to a great extent by the structure size of the dispersed phase. The scattering of light is dependent on the structure size. Therefore, clear or transparent compositions, according to this invention, are generally a single phase without droplets or structures, when viewed with the naked eye.

Furthermore, while emulsions are recognized as inherently unstable systems separating with time, microemulsions according to this invention, can be formed spontaneously, and are generally stable indefinitely.

It should be noted that true microemulsions of cyclic siloxanes in water are quite rare. Yet, classical methods of microemulsion formation have been known for many years in which a non-polar organic oil, water, a surfactant (S1), and a co-surfactant (S2), are mixed to form microemulsions, alleged to be thermodynamically stable. An adaptation of the classical method, coined the titration method, has even achieved some degree of notoriety in microemulsion circles, whereby organic oils, but not silicone oils, are added to a solution of a surfactant S1 and water to form two-phase mixtures. A co-surfactant (S2) is then slowly added with mixing, i.e., the titration, until the system becomes clear. It is said that microemulsions of particle size of 4 nanometer to about 20 nanometer can be formed in this fashion.

Advantage is taken of a titration method in this invention, in order to facilitate arriving at the production of silicone oil-in-water microemulsions, which can contain high molecular weight silicone polymers, with structures so small that they appear invisible to the naked eye, as a practical matter.

BRIEF SUMMARY OF THE INVENTION

This invention relates to microemulsions of polysiloxanes in water, and to methods for their preparation. Silicone oil-in-water microemulsions are prepared via the following steps:

1. A primary surfactant is dissolved in water.
2. A siloxane is added, and a two-phase mixture is formed.
3. With simple mixing, a co-surfactant is slowly added to the two-phase mixture, until a clear isotropic microemulsion of a siloxane-in-water is formed. These systems typically can have a mean particle size of less than about 20 nanometer, and a narrow particle size distribution.

Thus, siloxanes can, for example, be added to solutions containing ionic surfactants, such as dodecyltrimethyl ammonium bromide (DTAB) and sodium dodecyl sulfate (SDS), until a two-phase system is formed. A co-surfactant, such as 1-pentanol, is then titrated into the solution, until a clear, isotropic microemulsion results. Salts such as sodium chloride can also be included.

The system can be polymerized by the addition of, for example, a strong acid or a strong base ring-opening polymerization catalyst or a condensation polymerization catalyst. The use of such a thermodynamically stable pre-emulsion leads to a vastly simplified polymerization process. Some benefits, for example, include fast polymerization rates and high molecular weights. In some instances, a very low molecular weight polydispersity has been observed.

The invention, therefore, provides a method of making a thermodynamically stable, clear, single phase, silicone oil-in-water microemulsion, by (i) forming a two-phase mixture obtained by combining water, a siloxane, and a nonionic surfactant, a cationic surfactant, or an anionic surfactant; (ii) adding to the two-phase mixture a co-surfactant selected from the group consisting of monohydroxy alcohols, diols, and triols, until a thermodynamically stable, clear, single phase, pre-microemulsion containing the siloxane is formed; (iii) adding a polymerization initiator to the thermodynamically stable, clear, single phase, pre-microemulsion; (iv) heating the thermodynamically stable, clear, single phase, pre-microemulsion; (v) agitating the heated, thermodynamically stable, clear, single phase, pre-microemulsion; and (vi) allowing the siloxane to polymerize, until a thermodynamically stable, clear, single phase, microemulsion is formed containing a higher molecular weight silicone polymer.

The invention also provides a method of making a thermodynamically stable, clear, single phase, silicone oil-in-water microemulsion, by (i) forming a two-phase mixture obtained by combining water, a siloxane, and a nonionic surfactant, a cationic surfactant, or an anionic surfactant; and (ii) adding to the two-phase mixture a co-surfactant such as a monohydroxy alcohol, diol, or triol, until a thermodynamically stable, clear, single phase, microemulsion containing the siloxane is formed.

These and other features of the invention will become apparent from a consideration of the following detailed description.

BRIEF DESCRIPTION OF THE SEVERAL VIEWS OF THE DRAWING

Not applicable.

DETAILED DESCRIPTION OF THE INVENTION

Emulsion polymerization methods for making emulsions of high viscosity polymers involve starting with low viscosity polymer precursors, i.e., monomers, or reactive oligomers, which are immiscible in water; a surfactant to stabilize polymer precursor droplets in water; and a water soluble polymerization catalyst.

Typically, the catalyst is a strong mineral acid such as hydrochloric acid, or a strong alkaline catalyst such as sodium hydroxide. These components are added to water, the mixture is stirred, and polymerization is allowed to advance until the reaction is complete, or the desired degree of polymerization (DP) is reached, and an emulsion of the polymer is formed.

One example of such an emulsion polymerization process is described in U.S. Pat. No. 2,891,920 (Jun. 23, 1959), which shows a method of making aqueous emulsions of polydimethylsiloxanes, starting with precursor molecules of a polydimethylsiloxane.

Polydiorganosiloxane precursors generally used in such processes include cyclic siloxanes which are relatively insoluble in water, and which can be polymerized using an emulsion polymerization technique. These cyclic siloxanes generally are species having the formula:

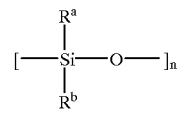

in which $R^a$ and $R^b$ denote methyl, ethyl, propyl, vinyl, allyl, or phenyl groups; and n is 3, 4, 5, or 6.

The cyclic siloxane precursors can be pure species, such as octamethylcyclotetrasiloxane, hexamethylcyclotrisiloxane, decamethylcyclopentasiloxane, tetramethyltetravinylcyclotetrasiloxane, and tetramethyltetraphenylcyclotetrasiloxane, or mixtures of the species can be used. One example of a mixture is a combination of cyclopolydimethylsiloxanes having three, four, and five siloxane units.

The reaction medium can include small portions of other organosilicon compounds containing hydrolyzable or silanol groups in the molecule, which are capable of polymerization. Some examples include amine functional silanes, vinyl functional silanes, and halogen-alkyl functional silanes. Silanes most often used include N-(2-aminoethyl)-3-(aminopropyl)trimethoxysilane, vinyltriethoxysilane, vinyltriacetoxysilane, and 3-chloropropyltrimethoxysilane.

The reaction medium generally comprises water, an effective amount of surfactant to stabilize polydiorganosiloxane droplets formed in the medium, and an effective amount of an initiator to polymerize the polydiorganosiloxane precursor.

According to the present invention, the emulsion polymerization process is utilized in preparing clear, stable, microemulsions, from an otherwise thermodynamically stable pre-emulsion which is formed with the aid of certain surfactant(s) S1 and co-surfactant(s) S2.

Thus, compositions according to this invention can be prepared by combining, and preferably contain 1–50 percent by weight of a silicone oil component; 50–98 percent by weight of water; 5–50 percent by weight of a surfactant or combination of surfactants S1; 5–15 percent by weight of a co-surfactant or combination of co-surfactants S2; optionally 0.01–1.0 percent by weight of a polymerization catalyst; and a sufficient quantity of neutralizing agent, including an excess of as much as 50 percent, necessary to neutralize the catalyst.

The silicone oil component of the composition can be a cyclic siloxane having the formula $\{R^1R^2SiO\}_x$ in which $R^1$ and $R^2$ are alkyl groups having 1–6 carbon atoms, aryl groups such as phenyl, or alkenyl groups such as vinyl and allyl, and x is 3–6. The silicone oil component of the composition can also be a short chain linear siloxane having the formula $R^c_3SiO\{R^d_2SiO\}_ySiR^c_3$ or the formula $HOR^c_2SiO\{R^d_2SiO\}_ySiR^c_2OH$ in which $R^c$ and $R^d$ are alkyl groups having 1–6 carbon atoms or aryl groups such as phenyl, and y is 0–10.

Some suitable cyclic siloxanes are hexamethylcyclotrisiloxane ($D_3$), a solid with a boiling point of 134° C. and the formula $\{(Me_2)SiO\}_3$; octamethylcyclotetrasiloxane ($D_4$) with a boiling point of 176° C., a viscosity of 2.3 mm²/s, and the formula $\{(Me_2)SiO\}_4$; decamethylcyclopentasiloxane ($D_5$) with a boiling point of 210° C., a viscosity of 3.87 mm²/s, and the formula $\{(Me_2)SiO\}_5$; dodecamethylcyclohexasiloxane ($D_6$) with a boiling point of 245° C., a viscosity of 6.62 mm²/s, and the formula $\{(Me_2)SiO\}_6$; and 1,3,5,7-tetravinyl-1,3,5,7-tetramethylcyclotetrasiloxane with the formula $\{(Me)(CH_2=CH)SiO\}_4$.

Some suitable short chain linear siloxanes are hexamethyldisiloxane (MM) with a boiling point of 100° C., viscosity of 0.65 mm²/s, and formula $Me_3SiOSiMe_3$; octamethyltrisiloxane (MDM) with a boiling point of 152° C., viscosity of 1.04 mm²/s, and formula $Me_3SiOMe_2SiOSiMe_3$; decamethyltetrasiloxane ($MD_2M$) with a boiling point of 194° C., viscosity of 1.53 mm²/s, and formula $Me_3SiO(Me_2SiO)_2SiMe_3$; dodecamethylpentasiloxane ($MD_3M$) with a boiling point of 229° C., viscosity of 2.06 mm²/s, and formula $Me_3SiO(Me_2SiO)_3SiMe_3$; tetradecamethylhexasiloxane ($MD_4M$) with a boiling point of 245° C., viscosity of 2.63 mm²/s, and formula $Me_3SiO(Me_2SiO)_4SiMe_3$; hexadecamethylheptasiloxane ($MD_5M$) with a boiling point of 270° C., viscosity of 3.24 mm²/s, and formula $Me_3SiO(Me_2SiO)_5SiMe_3$; and a silanol fluid with the formula $HO\{(CH_3)_2SiO\}_6H$. In these formulas, Me is used to represent a methyl group —$CH_3$.

The composition may contain a nonionic surfactant. Generally, it should be a non-silicon atom containing nonionic emulsifier. Most preferred are alcohol ethoxylates $R^3$—$(OCH_2CH_2)_aOH$, most particularly fatty alcohol ethoxylates. Fatty alcohol ethoxylates typically contain the characteristic group —$(OCH_2CH_2)_aOH$ which is attached to fatty hydrocarbon residue $R^3$ which contains about eight to about twenty carbon atoms, such as lauryl ($C_{12}$), cetyl ($C_{16}$) and stearyl ($C_{18}$). While the value of "a" may range from 1 to about 100, its value is typically in the range of about 12 to about 40.

Some examples of suitable nonionic surfactants are polyoxyethylene (4) lauryl ether, polyoxyethylene (5) lauryl ether, polyoxyethylene (23) lauryl ether, polyoxyethylene (2) cetyl ether, polyoxyethylene (10) cetyl ether, polyoxyethylene (20) cetyl ether, polyoxyethylene (2) stearyl ether, polyoxyethylene (10) stearyl ether, polyoxyethylene (20) stearyl ether, polyoxyethylene (21) stearyl ether, polyoxyethylene (100) stearyl ether, polyoxyethylene (2) oleyl ether, and polyoxyethylene (10) oleyl ether. These and other fatty alcohol ethoxylates are commercially available under trademarks and tradenames such as ALFONIC®, BRIJ, GENAPOL®, NEODOL®, SURFONIC®, and TRYCOL.

The composition may also contain a cationic surfactant. Cationic surfactants useful in the invention include compounds containing quaternary ammonium hydrophilic moieties in the molecule which are positively charged, such as quaternary ammonium salts represented by R'R"R'"R""N⁺ X⁻ where R', R", R'", and R"" are alkyl groups containing 1–30 carbon atoms, or alkyl groups derived from tallow, coconut oil, or soy; and X is halogen, i.e., chlorine or bromine. Most preferred are dialkyldimethyl ammonium salts represented by R'R"N⁺(CH₃)₂X⁻, where R' and R" are alkyl groups containing 12–30 carbon atoms, or alkyl groups derived from tallow, coconut oil, or soy; and X is halogen. Monoalkyltrimethyl ammonium salts can also be employed, and are represented by R'N⁺(CH₃)₃X⁻ where R' is an alkyl group containing 12–30 carbon atoms, or an alkyl group derived from tallow, coconut oil, or soy; and X is halogen.

Representative quaternary ammonium salts are dodecyltrimethyl amonium bromide (DTAB), didodecyldimethyl ammonium bromide, dihexadecyldimethyl ammonium chloride, dihexadecyldimethyl ammonium bromide, diocta-decyldimethyl ammonium chloride, dieicosyldimethyl ammonium chloride, didocosyldimethyl ammonium chloride, dicoconutdimethyl ammonium chloride, ditallowdimethyl ammonium chloride, and ditallowdimethyl ammonium bromide. These and other quaternary ammonium salts are commercially available under tradenames such as ADOGEN, ARQUAD, TOMAH, and VARIQUAT.

The composition may also contain an anionic surfactant. Examples of anionic surfactants include sulfonic acids and their salt derivatives; alkali metal sulfosuccinates; sulfonated glyceryl esters of fatty acids such as sulfonated monoglycerides of coconut oil acids; salts of sulfonated monovalent alcohol esters such as sodium oleyl isothionate; amides of amino sulfonic acids such as the sodium salt of oleyl methyl tauride; sulfonated products of fatty acid nitriles such as palmitonitrile sulfonate; sulfonated aromatic hydrocarbons such as sodium alpha-naphthalene monosulfonate; condensation products of naphthalene sulfonic acids with formaldehyde; sodium octahydro anthracene sulfonate; alkali metal alkyl sulfates such as sodium lauryl (dodecyl) sulfate (SDS); ether sulfates having alkyl groups of eight or more carbon atoms; and alkylaryl sulfonates having one or more alkyl groups of eight or more carbon atoms.

Commercial anionic surfactants useful in this invention include triethanolamine linear alkyl sulfonate sold under the tradename BIO-SOFT N-300 by the Stepan Company, Northfield, Ill. sulfates sold under the tradename POLYSTEP by the Stepan Company; and sodium n-hexadecyl diphenyloxide disulfonate sold under the tradename DOWFAX 8390 by The Dow Chemical Company, Midland, Mich.

The composition contains a co-surfactant. It may be a compound such as a monohydroxy alcohol, a diol, or a triol. Some preferred co-surfactants include 1-butanol, 1-pentanol, 1-decanol, 1-hexadecanol, ethylene glycol, propylene glycol, trimethylene glycol, and glycerol. Most preferred are the $C_4$ and $C_5$ alcohols for preparing fluid-type microemulsions, while the $C_6$ to $C_{10}$ alcohols are useful for preparing microemulsion gels.

If desired, the composition may contain an electrolyte such as sodium chloride or ammonium chloride, to increase the viscosity of the final product.

Catalysts capable of polymerizing siloxanes in the presence of water can be used in this invention. They include those materials generally known as condensation polymerization catalysts capable of cleaving siloxane bonds. Representative condensation polymerization catalysts include, but are not limited to, strong acids such as substituted benzenesulfonic acids, aliphatic sulfonic acids, hydrochloric acid, and sulfuric acid; and strong bases such as quaternary ammonium hydroxides, and metal hydroxides such as sodium hydroxide.

Condensation catalysts, which under certain conditions do not readily cleave siloxane bonds, can also be used in conjunction with siloxane precursors having a structure generally corresponding to $HO[(CH_3)_2SiO)]_zH$ where z generally has a value of 1 to about 30. Some examples of condensation catalysts of this type include weak organic acids and weak organic bases, or combinations thereof, such as blends of carboxylic acids and organic amines.

The method of stopping the reaction includes neutralization of the catalyst by addition of equal or slightly greater stoichiometric amounts of an acid or base, depending upon the type of catalyst. Strong or weak acids/bases may be used to neutralize the reaction. However, care must be taken when using a strong acid/base not to over neutralize, as it is possible to re-catalyze the reaction. It is preferred to neutralize with sufficient quantities of acids or bases so that the microemulsion has a pH of less than 7 when a cationic surfactant is present, and a pH of greater than 7 when an anionic surfactant is present. Representative neutralizing agents are phosphoric acid, glacial acetic acid, and triethanolamine.

EXAMPLES

The purpose of the following examples is to illustrate the invention in more detail.

Example 1

This example describes a general procedure used to prepare a number of microemulsions according to the method of the present invention. Conditions used in preparing each microemulsion according to the general procedure, and the characteristics of the resulting microemulsions of Examples 2–10, are summarized in accompanying Table 1.

The siloxane used in these examples was octamethylcyclotetrasiloxane ($D_4$). The cationic surfactant was dodecyltrimethyl ammonium bromide (DTAB) $CH_3(CH_2)_{11}N^+(CH_3)_3Br^-$. The anionic surfactant was sodium dodecyl sulfate (SDS), i.e., sodium lauryl sulfate $CH_3(CH_2)_{11}OSO_3^-Na^+$. The nonionic surfactant was an ethoxylated alcohol $R^3$—$(OCH_2CH_2)_aOH$ where $R^3$ was $C_{12}H_{25}$ and a was 5. It is abbreviated and shown in Table 1 as $C_{12}E_5$. The co-surfactants were primary amyl alcohol, i.e., 1-pentanol $CH_3(CH_2)_4OH$, and cetyl alcohol, i.e., 1-hexadecanol $C_{16}H_{33}OH$.

According to the general procedure, the siloxane, and a cationic surfactant, an anionic surfactant, or a nonionic surfactant, were added to a 20 milliliter glass vial, after the weight of each of the ingredients had been recorded using an analytical balance. A TEFLON® coated stirring bar was placed in the vial, and the vial was closed with a lid. The vial was placed onto a stirring plate. The co-surfactant was titrated into the vial dropwise, with mixing, until a thermodynamically stable, single phase, clear, pre-microemulsion, had formed at room temperature, i.e., 20–25 ° C.

At this point, the contents of the vial were transferred to a glass reaction vessel, where polymerization of the siloxane was catalyzed by adding to the vessel either a 50 percent by weight aqueous sodium hydroxide catalyst solution, or a 35 percent by weight aqueous hydrochloric acid catalyst solution, depending upon the nature of the surfactant. Generally, acid catalysts are used with anionic surfactants, alkaline catalysts are used with cationic surfactants, and acid or alkaline catalysts are used with nonionic surfactants. While other combinations do exist, they are considered less preferred.

The temperature of the reaction vessel was adjusted to about 50° C. Generally, addition of the catalyst to the clear microemulsion in the vessel causes the contents of the vessel to become cloudy. However, the reaction in the vessel is allowed to proceed to completion, whereupon the contents of the reaction vessel are neutralized with glacial acetic acid or triethanolamine.

The silicone polymer is recovered from the microemulsion by breaking the product using a salt. The silicone polymer is isolated and analyzed by Gel Permeation Chromatography (GPC). In the extraction procedure, 1.5 gram of anhydrous calcium chloride is added to a four ounce French square bottle, followed by 10 gram of the emulsion product to be broken. To the bottle is added 20 milliliter of methanol, and 25 milliliter of n-pentane. The bottle is shaken, and the top is unscrewed slowly to release any pressure in the bottle. The mixture is transferred to a 50 milliliter plastic centrifuge tube, and spun for about 10–15 minutes at 3000 rpm (314 radian per second). Some of the procedures may require longer periods of time in the centrifuge for separation of the layers. The top n-pentane layer containing the silicone polymer is then removed with a pipette, and transferred to a vial for analysis by GPC.

This otherwise standard emulsion salt break technique was modified to the extent that, instead of the n-pentane layer being pipetted into an aluminum pan to dry, the n-pentane layer was pipetted into a vial, to assure that any volatile siloxane species contained in the n-pentane layer did not evaporate prior to analysis of the sample via GPC.

In the accompanying Table 1, alpha (α) is used to indicate the weight percent of the siloxane oil÷the weight percent of the siloxane oil+the weight percent of water. Gamma (γ) indicates the weight percent of the cationic, anionic, or nonionic surfactant S1+the weight percent of the co-surfactant S2÷the weight percent of the siloxane oil+the weight percent of water+the weight percent of the cationic, anionic, or nonionic surfactant S1+the weight percent of the co-surfactant S2.

The data in Table 1 is based upon preparations of compositions having a total mass of ten gram, unless otherwise indicated. In Examples 3 and 7, the polymerization reaction was conducted in stages at two temperatures as noted in Table 1, i.e., the reaction medium was first heated to 70° C. and then it was cooled to 40° C.

The silicone polymer was characterized, and is shown in Table 1, by its polydispersity $DP_n$ and $DP_w$. In this regard, it is noted that the molecular weights of silicone fluids with a viscosity less than 5 $mm^2/s$ at 77° F./25° C. are generally quite precise, since such fluids are generally fractionally distilled products and relatively pure molecular species. Above about 5 $mm^2/s$, however, molecular weights are average values (i.e., $M_w$), since the fluids are residue products, and therefore contain a distribution of molecular sizes.

The molecular weight distribution of a polymeric sample describes the relative numbers of molecules of all molecular weight values. Averages of molecular weight such as the number-average molecular weight $M_n$, the weight-average molecular weight $M_w$, and the Z-average molecular weight $M_z$, are parameters most commonly used to describe the general shape of the molecular weight distribution. A peak weight-average molecular weight $M_w$ or $M_p$ is another parameter commonly used. One convenient measure of molecular weight distribution in a polymer is the ratio of its weight-average molecular weight $M_w$ to its number-average molecular weight $M_n$, i.e., $M_w/M_n$ or the polydispersity of the polymer. Generally, for perfectly uniform monodisperse polymers, the ratio is one.

Methods for measuring molecular weight distribution and molecular weight averages for silicones are the same as for other polymers. Gel Permeation Chromatography (GPC), sometimes termed size exclusion chromatography, is the most common, convenient, and useful method. This technique is based on separation of polymer molecules in a column packed with porous cross-linked gels, typically polystyrene, according to their size in solution.

Thus, when a polymer solution is eluted, species of higher molecular weight which permeate the porous polystyrene gel to a lesser degree than species of lower molecular weight, pass through the column more rapidly, and hence are eluted first. The system is calibrated and yields an estimated molecular weight distribution for a given sample. The only requirements are that the sample is soluble and stable in a suitable solvent, and that the sample components can be detected in the eluent by some means.

The system is calibrated by injecting dilute solutions of narrow dispersity standards of a known molecular weight. The retention volume or retention time of each standard is then plotted against the log molecular weight of the standard, and fitted to an equation for a curve. The molecular weight distribution values of a given polymer are then calculated and expressed as relative to that standard.

Polydispersity can be expressed in terms of $DP_n$ and $DP_w$ rather than $M_n$ and $M_w$, and this terminology has been used in Table 1. DP is the degree of polymerization in the silicone polymer, which indicates by way of example, a number "n" of repeating units in polymer species of the types $HO(Me_2SiO)_nH$ or $HOMe_2SiO(Me_2SiO)_nSiMe_2OH$ where Me is methyl.

Data for polydispersity of the silicone polymer in the microemulsion of Example 2 is not shown in Table 1. The data could not be obtained using standard extraction procedures indicating the stability of the microemulsion of Example 2.

Silicone polymers in the single phase compositions according to this invention most preferably have average droplet diameters of less than about 50 nanometer to provide optical clarity. The criteria used to determine clarity, and the term Clear in Table 1, is whether text can be read with the naked eye through a two centimeter diameter bottle filled with the microemulsion. This is a viable means of determining clarity as noted in *Microemulsions Theory and Practice*, Edited by Leon M. Prince, Academic Press, Inc., Pages 7–10, New York (1977), wherein the author states "Visual recognition of microemulsions should not be taken lightly. In fact, the microemulsion chemist should train himself carefully in this art. Use of sunlight rather than an artificial source of light is recommended. The eye is better than a microscope, because the limit of resolution of a light microscope in blue light is only about 0.1 μm, so that droplets smaller than 0.14 μm cannot be seen".

TABLE 1

| EXAMPLE | S1 | S2 | α | γ | Particle Size, μm | Appearance |
|---|---|---|---|---|---|---|
| 2 | SDS | $C_5H_{11}OH$ | 0.053 | 0.19 | 0.0050 | Clear |
| 3 | SDS | $C_5H_{11}OH$ | 0.053 | 0.19 | 0.0050 | Clear |
| 4 | SDS | $C_5H_{11}OH$ | 0.060 | 0.27 |  | Clear |
| 5 | DTAB | $C_5H_{11}OH$ | 0.100 | 0.27 | 0.0061 | Clear |
| 6 | DTAB | $C_5H_{11}OH$ | 0.220 | 0.37 | 0.0046 | Clear |
| 7 | SDS | $C_5H_{11}OH$ | 0.400 | 0.29 | 0.0289 | Clear |
| 8 | DTAB | $C_5H_{11}OH$ | 0.050 | 0.27 | 0.0043 |  |
| 9 | SDS | $C_5H_{11}OH$ | 0.050 | 0.17 | 0.0102 |  |
| 10 | DTAB | $C_{16}H_{33}OH$ | 0.050 | 0.24 |  |  |
| 11 | C12E5 | $C_5H_{11}OH$ | 0.100 | 0.24 | 0.0151 | Clear |

| EXAMPLE | Catalyst | Reaction Temp. °C. | $DP_n$ | $DP_w$ | Polydispersity |
|---|---|---|---|---|---|
| 2 | HCl | 50 |  |  |  |
| 3 | HCl | 70/40 | 21.0 | 32.0 | 1.510 |
| 4 | NaOH | 50 | 25.0 | 37.0 | 1.464 |
| 5 | NaOH | 50 | 33.0 | 57.0 | 1.725 |

TABLE 1-continued

| 6 | NaOH | 50 | 103.0 | 122.0 | 1.188 |
|---|---|---|---|---|---|
| 7 | HCl | 70/40 | 15.8 | 20.3 | 1.286 |
| 8 |  |  |  |  |  |
| 9 |  |  |  |  |  |
| 10 |  |  |  |  |  |
| 11 | NaOH | 22 | 34.0 | 54.0 | 1.605 |

Following the general procedure described in Example 1, some additional examples were carried out, for the purpose of illustrating the versatility of the invention, in the use of other types of alcohols and other types of siloxanes. Examples 12–21 are summarized in Table 2.

The Silanol used in Example 12 was a siloxane with a structure generally corresponding to $HO\{(CH_3)_2SiO\}_6H$. The siloxane used in Example 13 was cyclic siloxane species 1,3,5,7-tetravinyl-1,3,5,7-tetramethylcyclotetrasiloxane which has a structure generally corresponding to $\{(CH_3)(CH_2=CH)SiO\}_4$.

Example 17 is comparative and this is beyond the scope of the present invention. Its purpose is to show that alcohols having less than about four carbon atoms are not suitable for use as co-surfactants. As noted previously, the preferred co-surfactants according to the invention are the $C_4$ and $C_5$ alcohols for the preparation of fluid-type microemulsions, and $C_6$ to $C_{10}$ alcohols for preparing microemulsion gels. Generally, however, any alcohol containing 4 to 16 carbon atoms can be used. Example 21 shows that a salt such as sodium chloride can be included and that its presence is not deleterious.

TABLE 2

| EX. | S1 | S2 | α | γ | Siloxane | Particle Size, μm | Appearance |
|---|---|---|---|---|---|---|---|
| 12 | SDS | $C_5H_{11}OH$ | 0.027 | 0.13 | Silanol |  | Clear |
| 13 | SDS | $C_5H_{11}OH$ | 0.050 | 0.17 | MeVi Cyclic | 0.0440 | Clear |
| 14 | SDS | $C_5H_{11}OH$ | 0.050 | 0.17 | $MD_2M$ | 0.0118 | Clear |
| 15 | DTAB | $C_5H_{11}OH$ | 0.060 | 0.27 | D5 | 0.0066 | Clear |
| 16 | DTAB | $C_4H_9OH$ | 0.130 | 0.38 | D5 | 0.0099 | Clear |
| 17 | SDS | $C_3H_7OH$ | 0.050 | 0.54 | D4 | 5.2550 | Clear |
| 18 | SDS | $C_4H_9OH$ | 0.050 | 0.25 | D4 | 0.0131 | Clear |
| 19 | SDS | $C_6H_{13}OH$ | 0.050 | 0.20 | D4 |  | Clear Gel |
| 20 | SDS | $C_8H_{17}OH$ | 0.050 | 0.14 | D4 |  | Foamy Gel |
| 21 | DTAB NaCl | $C_5H_{11}OH$ | 0.100 | 0.21 | D4 | 0.0100 | Clear |

These single phase clear microemulsions have value in the personal care industry. It can be used alone, or blended with other cosmetic fluids, to form a variety of over-the-counter (OTC) personal care products.

Thus, it is useful in antiperspirants and deodorants since it leaves a dry feel. It is lubricious and improves the properties of skin creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers. It can be used in hair shampoos, hair. conditioners, hair sprays, mousses, permanents, depilatories, and cuticle coats, to enhance gloss and provide conditioning benefits. In cosmetics, it functions as a leveling and spreading agent for pigments in make-ups, color cosmetics, foundations, blushes, lipsticks, eyeliners, mascaras, oil removers, color cosmetic removers, and powders. It is also useful as a delivery system for oil and water-soluble substances such as vitamins. When incorporated into sticks, gels, lotions, aerosols, and roll-ons, the composition imparts a dry, silky-smooth, payout.

In addition, because these clear one phase microemulsions exhibit a variety of advantageous and beneficial properties such as (i) clarity, (ii) very small structure size, (iii) ultra-low interfacial tensions, (iv) the ability to combine properties of water and oil in a single homogeneous fluid, (v) shelf stability, and (vi) ease of preparation; they can have wide applications in other industrial areas such as textile finishing.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A method of making a thermodynamically stable, clear, single phase, silicone oil-in-water microemulsion, comprising sequentially (i) forming a two-phase mixture comprising water, a siloxane, and a nonionic surfactant, a cationic surfactant, or an anionic surfactant; (ii) adding to the two-phase mixture a co-surfactant selected from the group consisting of monohydroxy alcohols, diols, and triols, until a thermodynamically stable, clear, single phase, pre-microemulsion containing the siloxane is formed; (iii) adding a polymerization initiator to the thermodynamically stable, clear, single phase, pre-microemulsion; (iv) heating the thermodynamically stable, clear, single phase, pre-microemulsion; (v) agitating the heated, thermodynamically stable, clear, single phase, pre-microemulsion; and (vi) allowing the siloxane to polymerize, until a thermodynamically stable, clear, single phase, microemulsion is formed containing a silicone polymer.

2. A method according to claim 1 in which the siloxane is selected from the group consisting of cyclic siloxanes having the formula $\{R^1R^2SiO\}_x$ in which $R^1$ and $R^2$ are alkyl groups having 1–6 carbon atoms, aryl groups, or alkenyl groups, and x is 3–6; and linear siloxanes having the formula $R^c_3SiO\{R^d_2SiO\}_ySiR^c_3$ and the formula $HOR^c_2SiO\{R^d_2SiO\}_ySiR^c_2OH$ in which $R^c$ and $R^d$ are alkyl groups having 1–6 carbon atoms or aryl groups, and y is 0–10.

3. A method according to claim 1 in which the nonionic surfactant is an alcohol ethoxylate of the formula $R^3—(OCH_2CH_2)_aOH$ in which $R^3$ is a fatty hydrocarbon residue of 8–20 carbon atoms, and a has a value of 1–100.

4. A method according to claim 3 in which the nonionic surfactant is selected from the group consisting of polyoxyethylene (4) lauryl ether, polyoxyethylene (5) lauryl ether, polyoxyethylene (23) lauryl ether, polyoxyethylene (2) cetyl ether, polyoxyethylene (10) cetyl ether, polyoxyethylene (20) cetyl ether, polyoxyethylene (2) stearyl ether, polyoxyethylene (10) stearyl ether, polyoxyethylene (20) stearyl ether, polyoxyethylene (21) stearyl ether, polyoxyethylene (100) stearyl ether, polyoxyethylene (2) oleyl ether, and polyoxyethylene (10) oleyl ether.

5. A method according to claim 1 in which the cationic surfactant is a quaternary ammonium salt of the formula $R'R''R'''R''''N^+X^-$ in which R', R'', R''', and R'''' represent alkyl groups containing 1–30 carbon atoms, or alkyl groups derived from tallow, coconut oil, or soy; and X represents halogen.

6. A method according to claim 5 in which the cationic surfactant is a dialkyldimethyl ammonium salt of the formula $R'R''N^+(CH_3)_2X^-$ or a monoalkyltrimethyl ammonium salt of the formula $R'N^+(CH_3)_3X^-$ where R' and R'' represent alkyl groups containing 12–30 carbon atoms, or alkyl groups derived from tallow, coconut oil, or soy; and X represents halogen.

7. A method according to claim 5 in which the cationic surfactant is selected from the group consisting of dodecyltrimethyl ammonium bromide, didodecyldimethyl ammonium bromide, dihexadecyldimethyl ammonium chloride, dihexadecyldimethyl ammonium bromide, dioctadecyldimethyl ammonium chloride, dieicosyldimethyl ammonium chloride, didocosyldimethyl ammonium chloride, dicoconutdimethyl ammonium chloride, ditallowdimethyl ammonium chloride, and ditallowdimethyl ammonium bromide.

8. A method according to claim 1 in which the anionic surfactant is selected from the group consisting of sulfonic acids; salt derivatives of sulfonic acids; alkali metal sulfosuccinates; sulfonated glyceryl esters of fatty acids; salts of sulfonated monovalent alcohol esters; amides of amino sulfonic acids; sulfonated products of fatty acid nitrites; sulfonated aromatic hydrocarbons; condensation products of naphthalene sulfonic acids and formaldehyde; sodium octahydro anthracene sulfonates; alkali metal alkyl sulfates; ether sulfates having alkyl groups of at least eight carbon atoms; and alkylaryl sulfonates having one or more alkyl groups of at least eight carbon atoms.

9. A method according to claim 1 in which the co-surfactant is selected from the group consisting of 1-butanol, 1-pentanol, 1-decanol, 1-hexadecanol, ethylene glycol, propylene glycol, trimethylene glycol, and glycerol.

10. A method according to claim 1 in which the polymerization initiator is selected from the group consisting of substituted benzenesulfonic acids, aliphatic sulfonic acids, hydrochloric acid, sulfuric acid, quaternary ammonium hydroxides, and metal hydroxides.

11. A microemulsion prepared according to the method claimed in claim 1.

12. A method of making a thermodynamically stable, clear, single phase, silicone oil-in-water microemulsion, comprising the steps of (i) forming a two-phase mixture comprising water, a linear or cyclic siloxane, and a nonionic surfactant, a cationic surfactant, or an anionic surfactant; and (ii) adding to the two-phase mixture a co-surfactant selected from the group consisting of monohydroxy alcohols, diiols, and triols, until a thermodynamically stable, clear, single phase, microemulsion containing the siloxane is formed; the siloxane being selected form the group consisting of cyclic siloxanes having the formula $\{R^1R^2SiO\}_x$ in which $R^1$ is an alkyl group having 1–6 carbon atoms or an aryl group, $R^2$ is an alkenyl group, and x is a 3–6; and linear siloxanes having the formula $HOR^c_2SiO\{R^d_2SiO\}_ySiR^c_2OH$ in which $R^c$ and $R^d$ are alkyl groups having 1–6 carbon atoms or aryl groups, and y is 0–10.

13. A microemulsion prepared according to the method claimed in claim 12.

* * * * *